United States Patent [19]
Atwood

[11] Patent Number: 6,124,427
[45] Date of Patent: *Sep. 26, 2000

[54] ORGANOMETALLIC SINGLE SOURCE PRECURSORS FOR INORGANIC FILMS COATINGS AND POWDERS

[75] Inventor: David Allan Atwood, Fargo, N. Dak.

[73] Assignee: North Dakota State University

[ * ] Notice: This patent issued on a continued prosecution application filed under 37 CFR 1.53(d), and is subject to the twenty year patent term provisions of 35 U.S.C. 154(a)(2).

[21] Appl. No.: 08/831,289

[22] Filed: Mar. 31, 1997

[51] Int. Cl.$^7$ .................................. C08F 6/00; C08J 3/00
[52] U.S. Cl. ..................... 528/485; 528/395; 528/425; 528/503
[58] Field of Search .................................. 528/395, 425, 528/485, 503

[56] References Cited

U.S. PATENT DOCUMENTS

| | | | |
|---|---|---|---|
| 4,698,417 | 10/1987 | Morgan .................................. | 528/395 |
| 5,300,320 | 4/1994 | Barron et al. .......................... | 427/249 |

OTHER PUBLICATIONS

Lakhotia et al, "GaN Film Growth Using Single–Source Precursors", *Chem. Mater.* 1995 7, 546–552.

Atwood et al, "Dimeric Gallium and Indium Dialkylphosphido Complexes with Unusual Group 13–15 Stoichiometries", *Organometallics* 1993, 12, 3517–3521.

Hepp et al, "Sythesis and Decomposition Of a Novel Carboxylate Precursor To Indium Oxide", *Mat. Res. Soc. Symp. Proc.* vol. 335 ©1994.

Battiston et al, "Chemical vapour deposition and characterization of gallium oxide thin films", *Thin Solid Films* 279 (1996) 115–118.

Haanappel et al, Corrosion resistant coatings ($Al_2O_3$) produced by metal organic chemical vapour deposition using aluminium–tri–sec–butoxide.

Temple et al, "Formation of Aluminum Oxide Films from Aluminum Hexafluoroacetylacetonate at 350–450° C. *Journal of Electronic Materials*, vol. 19, No. 9 1990.

Maruyama et al, "Aluminum oxide thin films prepared by chemical vapor deposition from aluminum acetylacetonate", *Appl. Phys. Lett.* 60(3), Jan. 20, 1992.

Maruyama et al, Aluminum oxide thin films prepared by chemical vapor deposition from aluminum 2–ethylhexanoate, *Appl. Phys. Lett.* 58, May 13, 1991.

Kunicki et al, "Studies on the Reaction of Triethylaluminium with Methyl Alcohol", *Bulletin of the Polish Academy of Sciences Chemistry* vol. 33, No. 5–6, 1985.

Doub et al, "Oxidation of Triethylaluminum By Dry Air", *Am. Chem. Soc.* 69, 2714 (1947); 71, 2414 (1949).

Uetsuki et al, "A Study of the Structures of Aluminum Complexes with Isopropoxy and Methy Groups Using Pulsed NMR and Chemical Ionization Mass Spectrometry", *Bulletin Of The Chemical Society of Japan*, vol. 50(3), 673–679 (1977).

N. Ya. Turova et al, "Physico–Chemical and Structural Investigation of Aluminum Isopropoxide", *Inorg. Nucl. Chem.*, vol. 41, pp. 5–33.

*Primary Examiner*—Duc Truong

[57] ABSTRACT

The invention is directed to making inorganic materials consisting of a metal and a group 16 element in the stoichiometric ratio of 2:3 from single source precursors having the same 2:3 metal to heteroatom stoichiometric ratio.

In particular, the invention discloses a process for making aluminum oxide from single source precursors that have an aluminum to oxygen ratio of 2:3. The precursors are organoaluminum tetrametallic compounds containing organooxy bridging groups and organo terminal groups. As these compounds tend to be viscous liquids or oils, they can be applied to a substrate surface then pyrolyzed to eliminate the organic ligands and produce aluminum oxide in situ, without using gas phase deposition techniques.

13 Claims, 4 Drawing Sheets

ORGANOMETALLIC SINGLE SOURCE PRECURSORS FOR INORGANIC FILMS COATINGS AND POWDERS

FIELD OF THE INVENTION

This invention relates generally to producing inorganic materials consisting of a metal and a group 16 element in the stoichiometric ratio of 2:3 from organometallic single source precursors that have the same 2:3 stoichiometric ratio.

BACKGROUND OF THE INVENTION

There are many examples of inorganic compounds that combine a metal with a group 15 element in the stoichiometric ratio of 2:3. Many Transition and rare earth metals, for example, form oxides with this stoichiometry. The 2:3 stoichiomety is also observed for compounds that combine group 13 and group 16 elements, such as $M_2O_3$, $M_2S_3$, $M_2Se_3$ ant $M_2Te_3$, where M is aluminum, gallium, indium or thallium.

Many of these 2:3 stoichiometric ratio compounds have significant technical applications, especially when in the form of powders, films, coatings and electronic materials. As one example, aluminum oxide ($Al_2O_3$ or alumina), has been proposed for decoupling capacitor applications, as passivating layers and as radiation resistive films for semiconductor devices; with silicon dioxide, aluminum oxide can form insulator films for MOSFET (metal-oxide-semicorductor field effect transistor) and for MISFET (metal-insulator-semiconductor field effect transistor). Aluminum oxide powders, films and coatings are also useful in protecting materials against corrosion effects.

Several techniques are known for producing powders, films and coatings. Conventional organometallic chemical vapor deposition (OMCVD), for example, generally involves chemical reactions between two or more gas phase precursors. Frequently, these reactions occur at high temperatures, raise safety-related concerns and must be carefully controlled with respect to the stoichiometry of the reactants.

Some of these problems are addressed by film growing techniques which involve nct a reaction between two or more compounds but rather the pyrolysis of a single suitable precursor. Films of gallium nitride and gallium arsenide, for example, have been produced by single source precursor processes.

Generally, it is desirable to select single source precursors which contain elements and preexisting chemical bonds that also characterize the powder, film or coating of interest. Typically, single source precursors also contain organic groups or moieties, sometimes referred to as organic licands, that can be eliminated by heating or pyrolysis of the precursor.

With respect to the group 13/16 inorganic compounds discussed above, several single source precursors have been investigated in relation to making metal oxide films or coatings. For example, gallium oxide ($Ga_2O_3$) films have been made from gallium tris-hexafluoroacetylacetonate, aluminum oxide ($Al_2O_3$) films from aluminum hexafluoroacetylaicetonate, aluminum acetylacetonate, aluminum 2-ethylhexainoate, aluminum tri-sec-butoxide and aluminum tri-iscopropoxide and a mononuclear indium (III) benzoate has been investigated as a possible precursor for indium oxide ($In_2O_3$).

All of these precursors present disadvantages. For example, their use has been limited to gaseous phase deposition techniques. Furthermore, these precursors do not have the 2:3 metal to group 16 heteroatom ratio which is typical of the targeted inorganic material but instead contain excess oxygen.

OBJECTS OF THE INVENTION

Accordingly, it is an object of the invention to produce inorganic materials, having a 2:3 metal to group 16 heteroatom stoichiometric ratio, from organometallic single source precursors that have the same metal to group 16 heteroatom stoichiometric ratio.

It is another object of the invention to produce inorganic materials, having a 2:3 stoichiometric ratio between a group 13 metal and a group 16 heteroatom, from organometallic single source precursors that have the same group 13 metal to group 16 heteroatom stoichiometric ratio.

It is a further object of the invention to produce group 13 metal oxides, having a 2:3 stoichiometric ratio between the group 13 metal and oxygen, from single source precursors that have the same group 13 metal to oxygen stoichiometric ratio.

It is still a further object of the invention to provide inorganic materials of the 2:3 stoichiometry, particularly in the form of powders, films or coatings, from single source precursors of the same stoichiometry, at low temperatures and by means other than gas phase deposition techniques.

SUMMARY OF THE INVENTION

The above and other objects, which will become apparent to one skilled in the art upon a reading of this disclosure, are attained by the present invention one aspect of which is:

(1) A single source precursor process for making an inorganic material consisting of a metal and a group 16 element in a stoichiometric ratio of 2:3 comprising:

(A) providing an organometallic compound having at least one organic ligand and a 2:3 stoichiometric ratio between the metal and the group 16 element; and (B) decomposing said organometallic compound to eliminate the organic ligand and to produce said inorganic material.

Another aspect of the invention is:

A process for making a group 13 organometallic compound having a group 13 metal to oxygen stoichiometric ratio of 2:3 comprising:

(A) mixing a triorganometallic compound of a group 13 metal with a triorganooxymetallic compound of said group 13 metal in a solvent medium to form a reaction mixture;

(B) heating the reaction mixture at reflux temperature thereby reacting said triorganometallic compound with said triorganooxymetal compound; and (C) isolating from said solvent medium a group 13 organometallic compound having a group 13 metal to oxygen stoichiometric ratio of 2:3.

Still another aspect of the invention is a tetrametallic organoaluminum compound having an aluminum to oxygen stoichiometric ratio of 2:3 and comprising ethoxy bridging groups and isobutyl terminal groups.

As used herein, the terms "gas(eous) state deposition(s)" or "gas(eous) phase (deposition(s)" generally refer to methods whereby the precursor coming in contact with the substrate to be coated, or upon which a powder or film is to be deposited, is in the gaseous or vapor phase.

As used herein the term "tetrarietallic" generally refers to organometallic compounds heaving a three dimensional structure containing four metal atoms, M, all four M atoms belonging to the some group 13 element, with M=Al, Ga, In or Tl. Structurally, the tetrametallic compounds discussed herein contain a central six-coordinate M(III) atom connected to three surrounding four-coordinate M atoms through oxygen-containing bridging groups. More specifically, the central M atom is connected to each of the surrounding four-coordinate M atoms through two organooxy bridging groups. Two terminal groups are also bonded to each of the three surrounding four-coordinate M atoms. The general formula for these tetrametallic compounds is $[R_2M(mu-OR')_2]_3M$. As used herein the term "organic ligand(s)" generally refers to organic groups which, upon pyrolysis or photolysis of the organometallic single source precursor, are eliminated, generally in the form of compounds containing carbon and hydrogen, thereby producing the desired inorganic material.

As used herein, the terms "elements(s)" and "heteroatom (s)", as referring to the group 16 of the periodic table, are interchangeable.

As used herein, the terms "powders", "films" and "coatings" are interchangeable.

As used herein the terms "vicious liquid(s)" and "oil(s)" are interchangeable.

DETAILED DESCRIPTION OF THE INVENTION

Single source precursors present a number of advantages over conventional film deposition techniques. The presence of prevention bonds between the elements to be deposited generally ensures lower decomposition temperatures compared to conventional gas phase deposition techniques. The risk of damaging heat sensitive substrates is thereby reduced or eliminated and the invention can be practiced with heat sensitive substrates that may not be coated using conventional processes. Furthermore, except for carbon and hydrogen atoms, single source precursor depositions do not introduce into the process any extraneous atoms which are not desired in the intended inorganic material; consequently, films obtained from decomposing single source precursors are relatively frees of impurities.

As noted above, a number of technologically significant inorganic compounds present the 2:3 metal to heteroatom stoichiometric ratio. Using organometallic single source precursors that contain, not only the atoms desired in the targeted material, but also the desired 2:3 stoichiometry is thought to maximize the efficiency of the deposition process in that no atoms that compose the resulting material need to be eliminated. Since all the desired atoms in the precursor serve to form the material of interest, side reactions are kept to a minimum. Less disruption in film growth is expected with single source precursors having the same metal to heteroatom ratio as that of the intended inorganic material. Moreover, the organic products that are eliminated upon the decomposition of such precursors are generally gaseous and benign.

The invention relates to single source precursors that present all these stoichiometry-related advantages. In addition, by virtue of being viscous liquids or oils, some of these single source precursors can be used to make solid inorganic materials, in particular in the form of powders, films or coatings, by methods other than gas phase depositions.

Generally, the single source precursors of interest herein are organometallic compounds useful in making inorganic materials with a 2:3 stoichiometric ratio between a metal atom and a group 16 heteroatom, such as O, S, Se or Te. The essential characteristic of the precursors disclosed herein is their stoichiometry, which is identical to that of the desired inorganic material.

The invention can be practiced in relation to compounds combining a group 16 element and a metal, and may be particularly useful in the case of transition metals or metals from the lanthanide group. A preferred embodiment of the invention relates to single source precursors comprising group 13 metal atoms: Al, Ga, In, or Tl. Another preferred embodiment of the invention relates to single source Frecursors useful in producing group 13 metal oxides such as for example aluminum oxide, also known as $Al_2O_3$ or alumina.

One problem related to making inorganic materials from single source precursors that have the 2:3 stoichiometric ratio is the fact that this stoichiometry is unusual for some organometallic combinations, such as, for example, those between group 13 and group 16 elements. Predominaatly, group 13/16 complexes take 1:1, 1:2 or 1:3 stoicaiometries, these complexes appearing to favor symmetric dimeric, trimeric and tetrameric structures. The following are some general examples of these oligoiers having a group 13/16 stoichiometry of: 1:1, $[R_2MER']_n$; 1:2 $[RM(ER')_2]_n$; and 1:3 $[M(ER')_3]_n$ (where M=group 13 metal, E=group 16 heteroatom, n=2–4 and R and R'=organic groups. Dimeric (a), trimeric (b) and tetrame(ric (c) structures having the 1:3 stoichiometry are illustrated below in (1):

(c)

Symmetric structures are observed even with an unsymmetric mix of reagents, such as for example in a 2:3 ratio. This is due to the fact that such asymmetric 13/16 complexes tend to redistribute to form several symmetric species as depictd in (2) below:

(2a)

(2b)    (2c)

The invention discloses group 13/16 organometallic single source precursors that have the empirical formula shown in 2a. What is unique about the precursors disclosed herein is the fact that they maintain the 2:3 stoichiometry within one molecule. Generally, these precursors are tetrametallic although monomeric species and higher oligomers may also be envisioned to form depending on the steric requirements of either the R or R' group.

A further aspect of the invention is related to decomposing these single source precursors to form inorganic materials with the $M_2E_3$ formula.

The invention will be described in detail with reference to single source precursors comprising aluminum and oxygen, with the desired 2:3 stoichiometric ratio discussed above, and to the use of these precursors to make aluminum oxide, in particular in the form of powders, films or coatings.

Aluminum containing single source precursors may be prepared by reacting a triorganoaluminum compound ($AlR_3$), with a triorganooxyaluminum compound (also referred to as an aluminum triorganooxide compound or $Al(OR')_3$). Examples of suitable triorganoaluminum compounds include trialkyl- and triarylaluminum compounds. Trialkylaluminum compounds may include alkyl groups which are straight chains, as in the case of trimethyl- or triethylaluminum cr branched alkyl groups, as in the case of triisobutylaluminum. Similarly, triarylaluminum compounds may include phenyl, substituted phenyl groups, as well as other groups containing aromatic ring(s). Among suitable aluminum triorganooxides (or triorganooxyaluminum compounds) one may name aluminum trialkoxides or aluminum triaryloxides; in a preferred embodiment of the invention, the aluminum triorgaaooxide is triethoxyaluminum.

The invention can be extended to single source precursors comprising a group 13 metal other than aluminum by reacting the corresponding triorgano- and triorganooxy-compounds of the desired group 13 metal. For example a triorganogallium compound could be reacted with a trioganooxygallium compound. Similarly, by using the sulfur, selenium or tellurium analogues of the oxygen containing starting materials, the invention can be extended to precursors comprising group 16 elements other than oxygen.

The reactants are typically mixed in a solvent under an inert atmosphere, for example under nitrogen gas. Benzene, toluene, xylenes, other alkylbenzenes, other aromatics, or mixtures thereof are some examples of solvents that may be used to carey out the invention.

The resulting reaction mixture is heated, for example by connecting the vessel cortaining the reagent mixture to a vacuum line and refluxing for a period of time, usually of the order of several hours. Refluxing for two hours has been found adequate for all cases studied and refluxing for longer tines does not appear to have detrimental effects.

A typical example showing the reaction of $AlR_3$ with $Al(OEt)_3$ in toluene is presented in (3) below:

R = Me (1); Et (2); $^i$Bu (3)

Once the reaction is terminated, the product can be isolated, for example by removing the solvent under vacuum.

Typically, the products obtainei are viscous liquids or oils. Over a period of time, usually a day or two, some of the oils may exhibit a tendency to solidify. This process is reversible, for example by the addition of a small amount of solvent. The $^1H$ NMR spectra of the resulting solids are found close to being identical to those shown for the oils.

Mixing together two or more chemically distinct oils results in an viscous mixture that does not readily solidify at ambient temperature. For instance, a 1:1 combination of the oil 1, obtained from $Al(Me)_3$ and the oil 2, obtained from $Al(Et)$, was found to remain an oil over a period of at least several months.

Since a number of trialkylalumknum compounds are known to be pyrophoric and to react vigorously with reagents such as alcohols and water, the synthetic method disclosed herein presents significant safety-related advantages. In addition, the synthesis is efficient in that no gaseous byproducts are formed and all the reactant atoms are consumed to make the single source precursor of interest.

The structural analyses discussed below indicate that the organoaluminum compounds disclosed herein have the general molecular formula of $Al_4O_6R_6R'_6$. More particularly, these compounds appear to have a three dimensional tetrametallic structure, shown below as (I), whose formula can be generally written as [R₂Al(mu-OR')₂]₃Al, where R may be an alkyl or aryl group such as for example, methyl, ethyl or isobutyl and R' is also an alkyl or aryl group, for example ethyl.

(I)

Figure 1:
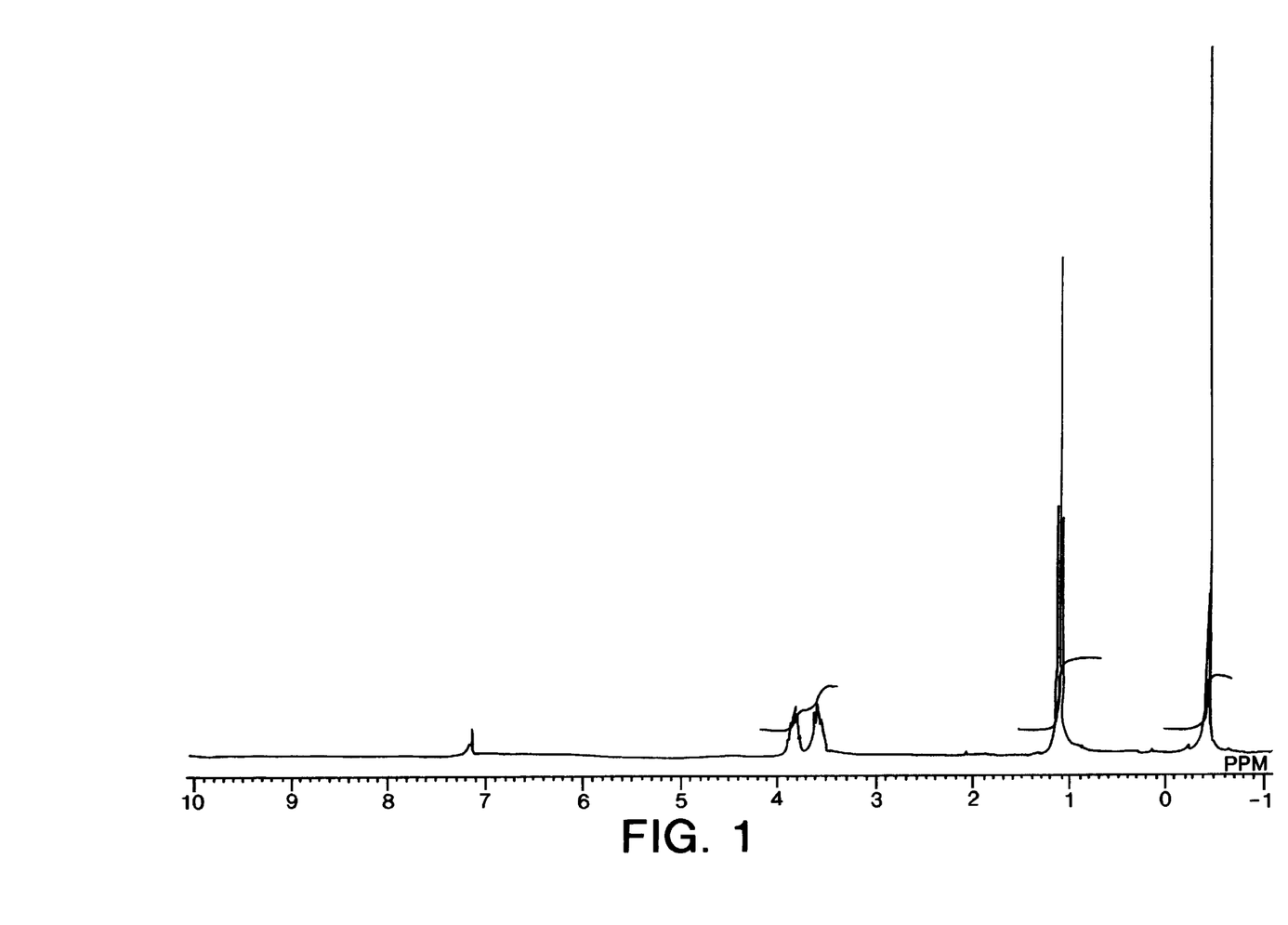
FIG. 1 is an $^1H$ NMR (Proton Nuclear Magnetic Resonance) spectrum for the compound obtained by reacting $Al(OEt)_3$ with $Al(Me)_3$.

The ¹H NMR spectra recorded for the oils 1 (shown in FIG. 1), 2 and 3, obtained by reacting Al(OEt)₃ with Al(Me)₃, Al(Et)₃ or Al($^i$Bu)₃, respectively, are very similar. A primary feature of the ¹H NMR data is the presence of one set of resonances for the Al—R group and one for the OCH₂CH₃ protons. The OCH₂ protons are manifested as two closely spaced multiplets. This behavior is consistent with the presence of distereotopic methylene groups which would be a consequence of a D3 symmetric molecule. The fact that two resonances are not observed for the CH₃ groups may be attributed to an averaging process or the coincidence of the two resonances.

Figure 2:
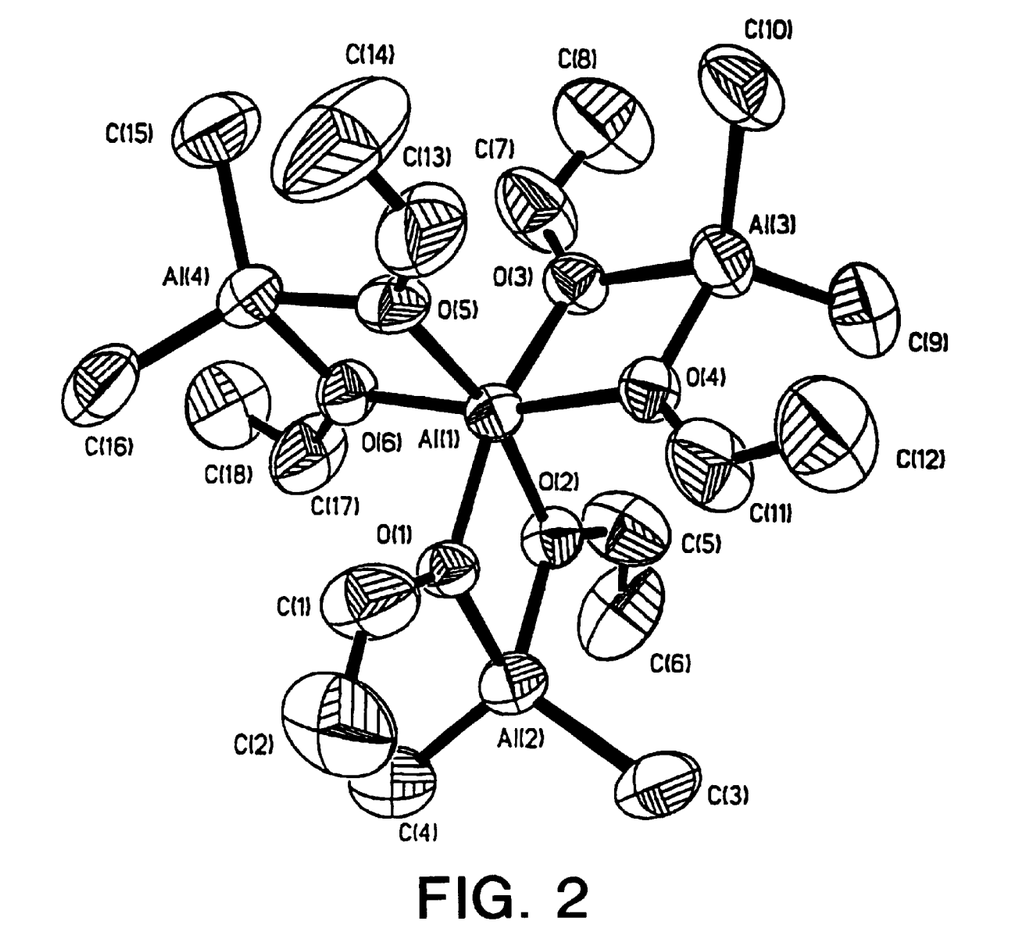
FIG. 2 is a molecular structure (ORTEP) and atom numbering scheme for $[Me_2Al(mu-OEt)_2]_3Al$.
Figure 3:
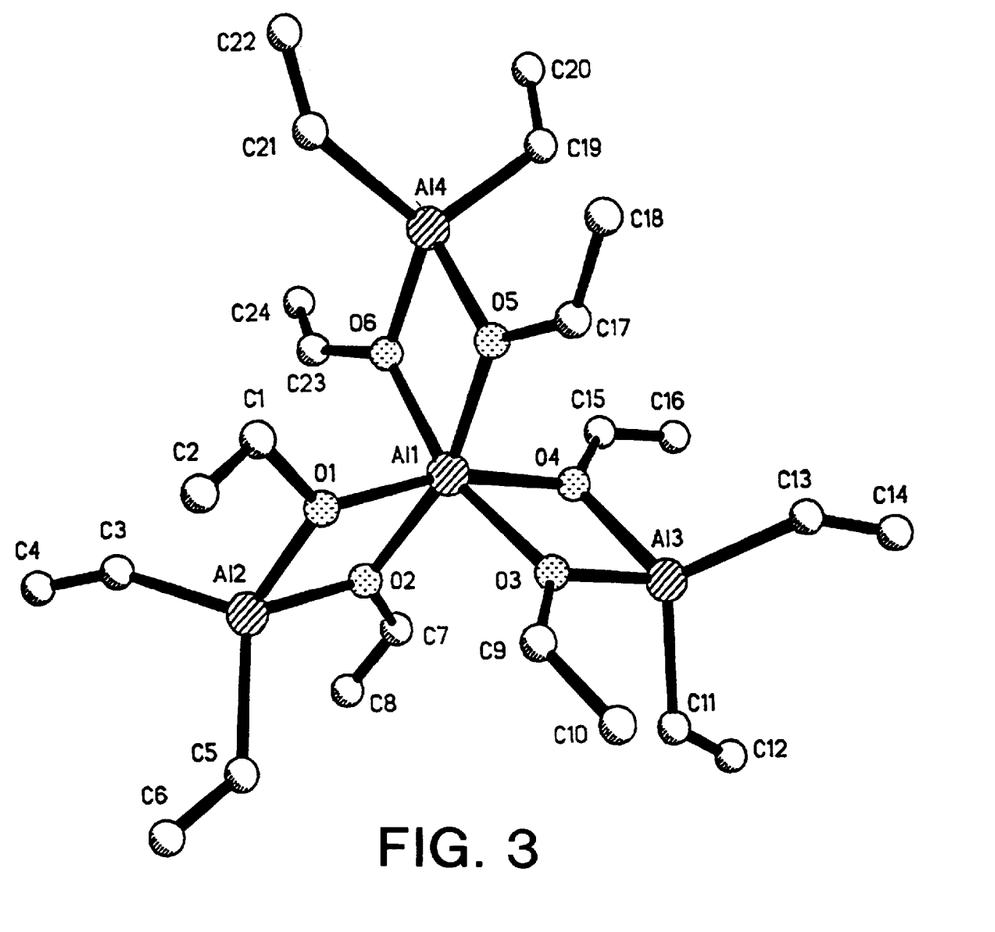
FIG. 3 is a molecular structure (isotropic) and atom numbering scheme for $[Et_2Al(mu-OET)_2]_3Al$ FIG. 4 rows the thermogravimetric analyses for the compounds obtained by reacting $Al(OEt)_3$ with $Al(Me)_3$, $Al(Et)_3$ and $Al(^tBu)_3$, respectively.

The oils 1 and 2, obtained from reacting Al(OEt)3 with Al(Me)₃ or with Al(Et)₃, respectively, solidified with enough crystallinity to permit X-ray crystallographic investigation. Molecular structures and atom numbering schemes for these two molecules are shown in FIGS. 2 and 3.

Compounds 1 and 2 form isomorphous tetrametallic structures. The central six-coordinate Al(III) atom is chelated in a bidentate fashion through the oxygen of the three R₂Al(OEt)₂- groups. The Al—O distances are longer around the central six-coordinate Al atom (average 1.9 Å) than for the terminal four-coordinate Al atom (average 1.8 A). This is in keeping with the increase in atomic radii of aluminum with increasing coordination number. This, in turn, leads to a relative increase in bond distances. All of the Al₂O₂ four member rings are planar. They idopt a propeller type arrangement around the central iluminum atom. The Al₂O₂ rings form dihedral angles of 59.2° (average) for 1 and 60.5° (average) for 2 with the coplanar aluminum atoms. These angles preclude an assignment of D$_{3h}$ for the point group.

The tetrametallic structural motif has been previously reported for aluminum. In most cases, the aluminum tetrametallic structures have the formula of Al₄O₁₂RR' and have alkoxy groups in both the bridging and the terminal positions. One example which has been studied in some detail is [($^i$PrO)₂Al(mu-O$^i$Pr)₂]₃Al. The Al₄O₁₂RR' tetrametallic compounds, however, do not possess the aluminum to oxygen ratio specific to aluminum oxide but contain excess oyxygen.

A few serendipitous observations of organoaluminum compounds similar to those disclosed here have been reported. Generally, these compounds have been observed in mixtures with other organoaluminum compounds, often also including tririers or dimers. In contrast to prior reports, the invention discloses a process for making these compounds directly, with high selectivity and in high yield. Moreover, the invention discloses tetrametallic organoalumirum compounds similar to I which have terminal alryl groups containing more than two carbon atoms.

The organoaluminum compounds disclosed herein can be used to produce aluminum oxide. According to a preferred embodiment, the decomposition reaction can be carried out by heating the single source precursors to a temperature and for a period of time sufficient for the elimination of the organic ligands. The pyrolysis process is shown in (4) below:

(4)

Decomposition of the single source precursors can be effected through other processes, for example by photolyzing the organoaluminum compounds disclosed herein using electromagnetic radiation of such intensity and within such a wavelength region as necessary to break chemical bonds and eliminate the organic ligands. In addition to using conventional photolysis techniques, one- or multi-photon laser induced photolysis may also be used to effect the desired decomposition.

Figure 4:
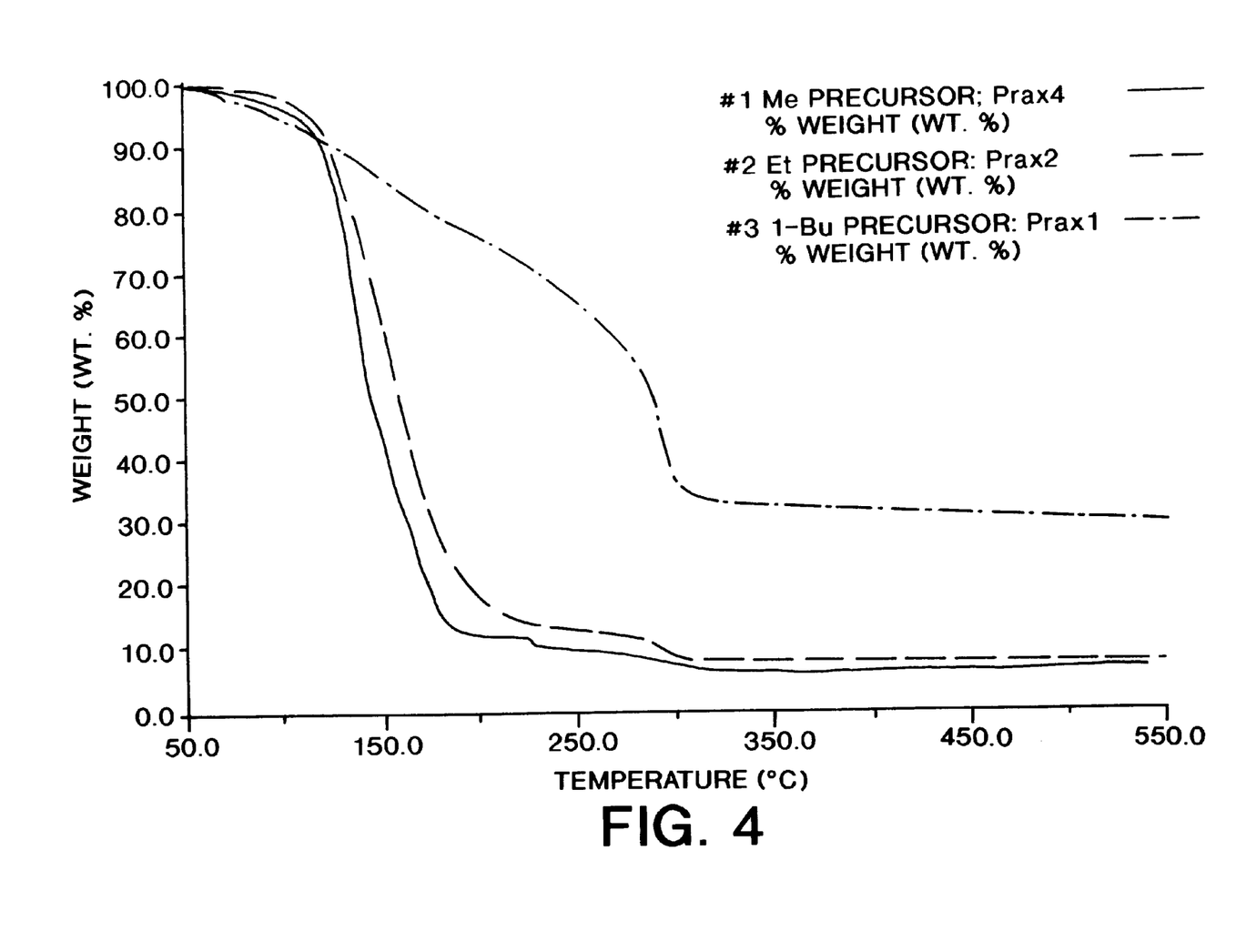

The usefulness of the organoalumninum compounds disclosed herein as single source precursors for aluminum oxide can be discussed in relation to FIG. 4. The Figure presents the results of thermogravimetric analyses, conducted on a Perkin-Elmer analyzer, and undertaken to determine whether the compounds decompose fully by eliminating the organic ligands and, if so, at what temperature.

As shown in FIG. 4, Compounds 1 and 2 display similar behavior, showing the primarily mass loss event as taking place over the temperature range of roughly 125° C. to 200° C. The calculated ideal remaining mass for compounds 1 and 2 (as calculated for Al₄O₆) is about 40% [(43% for 1 and 36% for 2)] of the initial mass of the sample. The observed remaining mass percent for these two compounds, however, is below 20% of the initial sample mass. This is indicative of a loss of material from the TGA sample, possibly in the form of boiling or of sublimation.

Compound 3 decomposes over a broader temperature range which ends at approximately 300° C. In contrast to compounds 1 and 2, however, mass loss for compound 3 results in a remaining mass closer to the ideal value of 28%, as calculated for Al₄O₆. It appears therefore that for compound 3 decomposition occurs prior to the boiling or sublimation point.

While all three compounds have the potential of forming aluminum oxide at relatively low temperatures, compound 3, which is accompanied by the least losses of material, brings additional cost related benefits to the economics of the decomposition process.

Although the invention is described in detail with respect to organometallic compounds comprising aluminum and oxygen, it can be practiced with other single source precursors having the desired 2:3 metal to group 16 heteroatom stoichiometric ratio. Accordingly, single source precursors comprising aluminum and sulfur, selenium or tellurium in the 2:3 ratio, as well as single source precursors which combine a metal other than aluminum with a group 16 element, also in the desired 2:3 metal to heteroatom stoichiometry, can be decomposed to eliminate the organic ligands and produce the corresponding 2:3 inorganic material.

The single source precursors having the 2:3 metal to heteroatom ratio can be used to make $M_2E_3$ inorganic materials, in particular in the form of powders, films and coatings, through conventional gaseous state deposition techniques, as disclosed in the prior art.

When these single source precursors are liquids, viscous liquids or oils they present the additional advantage of being useful for making $M_2E_3$ powders, films or coatings in situ, by methods; other than gas phase deposition.

To produce coatings by methods other than gaseous state deposition, a liquid or oily single source precursor can be applied, in one or more layers, onto a desired substrate prior to its decomposition and the elimination of organic ligands. Substrates may be made of various materials as long as these materials would not be damaged under the heating conditions required to decompose the single source precursor. Some examples of suitable substrate materials include but are not limited to metals, glass, silicon, alloys, ceramics, electronic materials, some plastics, thermoset polymeric compounds and others. Generally, it is found that once applied to the substrate, the oils adhere to the surface of the substrate.

When more than one layer of liquid or oil is applied, the coated substrate may be heated repeatedly; for example, the substrate may be heated after each layer is applied.

Painting the precursor upon a surface of interest is one way in which the liquids or oils can be applied onto substrates in order to form aluminum oxide films, coatings or powders. Another approach involves dipping the substrate into the single source precursor liquid or oil followed by heating the coated substrate.

It may also be possible to atomize liquids or viscous precursors, with the help of a suitable atomizing fluid or process, and spray them onto the substrate. In addition, the oils or liquids can be first dissolved in a suitable volatile solvent and the resulting solution sprayed upon the substrate. Subsequent heating would then effect not only the decomposition of the precursor to that desired inorganic material but also the evaporation of solvent. If desired, the spraying and heating can be repeated.

It may be desired to apply the liquid or oily precursors to a substrate by combining more than one of the techniques described above. It may also be desired to apply more than one oil or liquid to a substrate, either in a mixture or sequentially.

As already noted, the aluminum tetrametallic single source precursors discussed above are viscous liquids. Even when the viscous single source precursors exhibit a tendency to solidify, it may be possible to increase the longevity or shelf life of the oils. For example, a single source precursor that remains in a viscous state for at least several months can be obtained by mixing two or more chemically distinct organoaluminum compounds while in their viscous state.

In the transformation of the tetrametallic organoaluminum compounds to alumina, temperatures, for example, in the range of 180° C. to 400° C. appear effective and the resulting coatings were shown to consist primarily of aluminum and oxygen.

The following examples are presented for illustrative and comparative purpose. They are not intended to be limiting.

EXAMPLE 1

This example provides a detailed description of the synthetic procedures followed to make several single source precursors. All manipulations are conducted using vacuum line techniques in conjunction to an inert atmosphere glove box. All solvents are rigorously dried prior to use.

For the characterization of the compounds obtained, the NMR data were obtained on JEOL-GSX-400 and -270 instruments at 270.17 ($^1H$) and 62.5($^{13}C$)MHz. Chemical shifts are reported relative to SiMe4 and are in ppm. Elemental analyses were obtained on a Perkin-Elmer 2400 analyzer. Infrared data were recorded as KBr pellets on a Matheson Instruments 2020 galaxy Series spectrometer and are reported in cm-1. X-ray powder diffraction data were collected on a Philips diffractometer.

$[Me_2Al(mu-OEt)_2]_3Al$ (1): To a stirred suspension of aluminum triethoxide (30.83 mmol, 5.000 g) in toluene (30 mL) at 25° C. is added a solution of trimethylaluminum (30.83 mmol, 2.223 g) in toluene (30 mL). The mixture is then brought to reflux and the solid goes into solution after 20 minutes. the solution is refluxed for a total of 4 hours, cooled to 25° C. and filtered to remove a small amount of insoluble material. The volatiles are removed; under reduced pressure yielding a nearly colorless, viscous oil (6.742 g, 93%) which crystallizes in a period of time from 1 day to 3 months. Mp 162–65° C. $^1H$ NMR ($C_6D_6$): delta –0.43 (s, 18H, AlC$\underline{H}_3$), 1.12 (t, 18H, OCH$_2$C$\underline{H}_3$), 3.39 (m, 6H, OC$\underline{H}_aH_b$), 3.83 (m, 6H, OCH$_a\underline{H}_b$). IR (KBr): nu 2984 s, 2943 m, 2906 m, 2818 m, 1471 m, 1390 m, 1197 s, 1103 s, 1060 s, 900 s, 680 s(br), 582 s, 523m.

$[Et_2Al(mu-OEt)_2]_3Al$ (2): The procedure is as for (1) using aluminum triethoxide (30.83 mmol, 5.000 g), toluene (60 mL) and triethylaluminum (30.83 mmol, 21.336 g of a 1M solution in hexanes) yielding a nearly colorless, viscous oil (8.308 g, 98%). This oil also crystallizes in a period of time from 3 days to several months. Mp 124–27° C. $^1H$ NMR ($C_6D_6$): delta 0.17 (m, 12H, AlC$\underline{H}_2$CH$_3$), 1.12 (t, 18H, AlCH$_2$C$\underline{H}_3$O), 1.38 (t, 18 H, OCH$_2$C$\underline{H}_3$), 3.56 (m, 6H, OC$\underline{H}_aH_b$), 3,78 (m, 6H, OCH$_a\underline{H}_b$). IR (KBr): nu 2978 s, 2939 s, 2911 s, 2817 m, 1452 m, 1408 s, 1321 m, 1195 m, 1165 m, 1101 s, 1060 s, 896 s, 640 s (br).

$[^iBu_2Al(mu-OEt)_2]_3Al$ (3): The procedure is as for (1) using aluminum triethoxide (30.83 mmol, 5.000 g), toluene (60 mL), and truisobutylalumnum (30.83 mmol, 6.115 g) yielding a nearly colorless, viscous oil (19.528 g, 95%). Crystalline material was never obtained from this reaction. $^1H$ NMR ($C_6H_6$): delta 0.15 (d, 12 H, AlC$\underline{H}_2$CH(CH$_3$)$_2$), 1.08 (d 18H ALCH$_2$CH(C$\underline{H}_3$)$_2$), 1.19 (t, 18H, OCH$_2$C$\underline{H}_3$), 2.01 (m, 6H, AlCH$_2$C$\underline{H}$(CH$_3$)2), 3.73 (m, 6H, OC$\underline{H}_aH_b$), 3.92 m, (6H, OCH$_a\underline{H}_b$). IR (neat): n 2949 s, 2866 s, 2773 m, 1462 s, 1390 s, 1359 s, 1340 m, 1160 s, 1059 s 896 s, 871 s(br).

EXAMPLE 2

The oils 1 and 2, obtained from reacting $Al(OEt)_3$ with $Al(Me)_3$ or with $Al(Et)_3$, respectively, solidified with enough crystallinity to permit X-ray crystallographic investigation. Single crystals suitable for X-ray analysis were obtained from samples which were allowed to sit undisturbed, at 25° C., for 3 months in the case of compound 1 and for 5 days for compound 2.

Molecular structures and atom numbering schemes for these two molecules are shown in FIGS. 2 and 3. Tables 1–4 contain relevant positional parameters and bond lengths and angle information.

In each of the data collections the check reflections indicated a less than 5% decrease in intensity over the course of data collection and hence, no correction was applied. All calculations were performed on a personal computer using the Siemens software package, SHELXTL-Plus. The structures were solved by direct methods and successive interpretation of difference Fourier maps, followed by least-squares refinement. All non-hydrogen atoms were refined anisotropically. The hydrogen atoms were included in the refinement in calculated positions using fixed isotropic parameters. With the exception of having a weakly diffracting crystal for 2, which exacerbated the problem of ethyl group motion, there were no other problems in structure solutions.

A summary of data collection parameters and structure solution variables is given in Table 5. Table 6 shows selected bond lengths and angles for compounds 1 and 2 and for some related compounds.

TABLE 1-continued

Atomic coordinates ($\times 10^5$) and equivalent isotropic displacement cooefficients ($Å^2 \times 10^4$) for 1

| Atom | x | y | z | U(eq) |
|---|---|---|---|---|
| C(9) | 70185(128) | −13909(120) | 31349(64) | 1516(88) |
| C(10) | 47276(104) | −2398(130) | 35524(57) | 1338(76) |
| C(11) | 64308(133) | 17041(151) | 25607(62) | 1435(84) |
| C(12) | 57438(166) | 11452(164) | 21673(64) | 2171(132) |
| C(13) | 52288(132) | 29941(163) | 38175(79) | 1595(103) |
| C(14) | 44433(140) | 35209(208) | 40463(79) | 2607(176) |
| C(15) | 64521(118) | 29109(141) | 54598(56) | 1505(87) |
| C(16) | 73152(118) | 51623(122) | 47773(60) | 1349(81) |
| C(17) | 94308(119) | 27468(161) | 48405(58) | 1417(88) |
| C(18) | 96733(120) | 29016(153) | 54457(62) | 1613(96) |

TABLE 2

Bond Lengths (Å) Angles (°) for 1

| | | | | | | |
|---|---|---|---|---|---|---|
| Al(1)–O(1) | 1.896(8) | Al(3)–O(3) | 1.816(8) | O(3)–C(7) | 1.388(18) |
| Al(1)–O(2) | 1.904(8) | Al(3)–O(4) | 1.815(8) | O(4)–C(11) | 1.405(16) |
| Al(1)–O(3) | 1.891(8) | Al(3)–C(9) | 1.920(15) | O(5)–C(13) | 1.397(17) |
| Al(1)–O(4) | 1.900(7) | Al(3)–C(10) | 1.944(13) | O(6)–C(17) | 1.396(15) |
| Al(1)–O(5) | 1.888(9) | Al(4)–O(5) | 1.807(8) | C(1)–C(2) | 1.271(25) |
| Al(1)–O(6) | 1.904(7) | Al(4)–O(6) | 1.813(9) | C(5)–C(6) | 1.395(21) |
| Al(2)–O(1) | 1.815(8) | Al(4)–C(15) | 1.941(15) | C(7)–C(8) | 1.345(23) |
| Al(2)–O(2) | 1.813(9) | Al(4)–C(16) | 1.923(15) | C(11)–C(12) | 1.280(22) |
| Al(2)–O(3) | 1.952(12) | O(1)–C(1) | 1.380(17) | C(13)–C(14) | 1.270(26) |
| Al(2)–O(4) | 1.960(13) | O(2)–C(5) | 1.383(17 | C(17)–C(18) | 1.376(19) |
| O(1)–Al(1)–O(2) | 75.8(3) | O(2)–Al(2)–C(4) | 115.4(5) | Al(2)–O(2)–C(5) | 125.6(9) |
| O(1)–Al(1)–O(3) | 165.7(4) | O(3)–Al(2)–C(4) | 113.9(6) | Al(1)–O(3)–Al(3) | 102.7(4) |
| O(2)–Al(1)–O(3) | 95.0(4) | O(3)–Al(3)–C(4) | 79.4(4) | Al(1)–O(3)–C(7) | 130.8(8) |
| O(1)–Al(1)–O(4) | 94.3(3) | O(3)–Al(3)–C(9) | 115.0(5) | Al(3)–O(3)–C(7) | 125.7(8) |
| O(2)–Al(1)–O(4) | 96.2(3) | O(4)–Al(3)–C(9) | 115.3(6) | Al(1)–O(4)–Al(3) | 102.4(4) |
| O(3)–Al(1)–O(4) | 75.4(3) | O(3)–Al(3)–C(10) | 114.2(5) | Al(1)–O(4)–C(11) | 130.5(8) |
| O(1)–Al(1)–O(5) | 94.6(4) | O(4)–Al(3)–C(10) | 114.5(5) | Al(3)–O(4)–C(11) | 126.7(8) |
| O(2)–Al(1)–O(5) | 165.7(4) | O(9)–Al(3)–C(10) | 114.0(7) | Al(1)–O(5)–Al(4) | 102.3(4) |
| O(3)–Al(1)–O(5) | 96.2(4) | O(5)–Al(4)–O(6) | 80.2(4) | Al(1)–O(5)–C(13) | 130.6(9) |
| O(4)–Al(1)–O(5) | 95.2(3) | O(5)–Al(4)–C(15) | 114.9(5) | Al(4)–O(5)–C(13) | 126.9(9) |
| O(1)–Al(1)–O(6) | 96.7(3) | O(6)–Al(4)–C(15) | 114.6(5) | Al(1)–O(6)–Al(4) | 101.5(4) |
| O(2)–Al(1)–O(8) | 94.3(3) | O(5)–Al(4)–C(16) | 115.2(5) | Al(1)–C(6)–C(17) | 130.6(8) |
| O(3)–Al(1)–O(6) | 94.9(6) | O(6)–Al(4)–C(16) | 113.6(5) | Al(4)–O(6)–C(17) | 126.0(8) |
| O(4)–Al(1)–O(6) | 166.3(4) | C(15)–Al(4)–C(16) | 114.2(7) | O(1)–C(1)–C(2) | 127.1(16) |
| O(5)–Al(1)–O(6) | 75.9(3) | Al(1)–O(1)–Al(2) | 102.1(4) | O(2)–C(5)–C(6) | 120.5(13) |
| O(1)–Al(2)–O(2) | 80.1(4) | Al(1)–O(1)–C(1) | 132.5(9) | O(3)–C(7)–C(8) | 122.7(14) |
| O(1)–Al(2)–C(3) | 115.2(5) | Al(2)–O(1)–C(1) | 125.3(9) | O(4)–C(11)–C(12) | 123.8(15) |
| O(2)–Al(2)–C(3) | 113.8(5) | Al(1)–O(2)–Al(2) | 101.9(4) | C(5)–C(13)–C(14) | 125.8(16) |
| O(1)–Al(2)–C(4) | 114.3(5) | Al(1)–((2)–C(5) | 131.0(8) | O(6)–C(17)–C(18) | 119.5(12) |

TABLE 1

Atomic coordinates ($\times 10^5$) and equivalent isotropic displacement cooefficients ($Å^2 \times 10^4$) for 1

| Atom | x | y | z | U(eq) |
|---|---|---|---|---|
| Al(1) | 76297(28) | 20708(30) | 38113(14) | 646(13) |
| Al(2) | 94582(32) | 27869(36) | 31606(16) | 849(16) |
| Al(3) | 63514(37) | −503(38) | 34631(18) | 946(18) |
| Al(4) | 70681(36) | 35003(39) | 47700(18) | 947(18) |
| O(1) | 80962(58) | 33225(61) | 33547(29) | 652(29) |
| O(2) | 90848(61) | 15778(68) | 36112(31) | 741(31) |
| O(3) | 72406(61) | 5979(63) | 41029(34) | 767(32) |
| O(4) | 66989(57) | 13471(63) | 31557(30) | 710(31) |
| O(5) | 63952(65) | 29039(68) | 40673(33) | 810(33) |
| O(6) | 82775(65) | 26692(69) | 45689(29) | 811(32) |
| C(1) | 76308(147) | 44147(135) | 32155(74) | 1377(93) |
| C(2) | 80377(152) | 52037(136) | 29118(88) | 1942(134) |
| C(3) | 94279(111) | 23918(115) | 23240(48) | 1186(69) |
| C(4) | 108235(108) | 36932(132) | 35015(61) | 1408(83) |
| C(5) | 96218(126) | 4968(136) | 36571(77) | 1365(91) |
| C(6) | 108229(132) | 4075(144) | 36821(69) | 1628(101) |
| C(7) | 73934(152) | 1530(142) | 46766(73) | 1473(96) |
| C(8) | 70308(158) | −9193(166) | 48059(67) | 2013(125) |

TABLE 3

Atomic coordinates ($\times 10^5$) and equivalent isotropic displacement cooefficients ($Å^2 \times 10^4$) for 1

| Atom | x | y | z | U(eq) |
|---|---|---|---|---|
| Al(1) | 2279(7) | 1933(7) | 1127(3) | 98(4) |
| Al(3) | 3625(9) | −7(9) | 1382(5) | 131(5) |
| Al(2) | 2704(9) | 3379(9) | 251(5) | 145(6) |
| Al(4) | 499(9) | 2415(9) | 1747(4) | 133(5) |
| O(1) | 1635(15) | 2491(15) | 439(8) | 113(9) |
| O(2) | 3338(17) | 2838(19) | 899(10) | 142(12) |
| O(3) | 2734(19) | 642(19) | 851(9) | 126(12) |
| O(4) | 3236(14) | 1221(16) | 1709(8) | 114(9) |
| O(5) | 940(14) | 1383(16) | 1287(7) | 114(10) |
| O(6) | 1737(21) | 2962(15) | 1579(10) | 130(12) |
| C(1) | 516(36) | 2689(33) | 199(12) | 210(28) |
| C(2) | 262(28) | 2681(32) | −312(13) | 270(30) |
| C(3) | 2518(40) | 4882(27) | 266(16) | 279(34) |
| C(4) | 2713(40) | 5770(26) | 166(21) | 472(60) |
| C(5) | 3394(35) | 2945(32) | −348(14) | 223(26) |
| C(6) | 3286(42) | 3223(42) | −829(14) | 461(64) |
| C(7) | 4436(46) | 2958(38) | 1168(24) | 282(42) |
| C(8) | 5058(38) | 3506(41) | 1009(20) | 444(60) |

TABLE 3-continued

Atomic coordinates (×10⁵) and equivalent isotropic displacement cooefficients ($Å^2 \times 10^4$) for 1

| Atom | x | y | z | U(eq) |
|---|---|---|---|---|
| C(9) | 2569(36) | 319(31) | 345(21) | 234(38) |
| C(10) | 2876(29) | −617(30) | 125(12) | 228(28) |
| C(11) | 5175(32) | −10(31) | 1248(18) | 232(29) |
| C(12) | 5918(39) | −375(43) | 1490(21) | 547(73) |
| C(13) | 3046(52) | −1350(42) | 1624(20) | 291(41) |
| C(14) | 3341(44) | −2099(43) | 1772(22) | 423(68) |
| C(15) | 3514(25) | 1425(31) | 2255(13) | 188(22) |
| C(16) | 4121(27) | 960(31) | 2646(11) | 283(32) |
| C(17) | 517(25) | 432(27) | 1235(13) | 179(23) |
| C(18) | −462(26) | 57(24) | 1319(12) | 237(38) |
| C(19) | 584(31) | 1883(41) | 2505(19) | 260(37) |
| C(20) | 260(46) | 2285(42) | 2860(19) | 451(63) |
| C(21) | −818(31) | 3177(39) | 1476(14) | 192(24) |
| C(22) | −1615(37) | 3422(48) | 1606(22) | 640(93) |
| C(23) | 1976(34) | 3960(42) | 1679(16) | 228(36) |
| C(24) | 2094(37) | 4595(37) | 2091(16) | 403(48) |

TABLE 4

Bond Lengths (Å) Angles (°) for 2

| Al(1)–O(1) | 1.875(20) | Al(2)–C(3) | 1.856(35) | C(1)–C(2) | 1.240(43) |
|---|---|---|---|---|---|
| Al(1)–O(2) | 1.852(25) | Al(2)–C(5) | 1.874(41) | C(3)–C(4) | 1.148(49) |
| Al(1)–O(3) | 1.837(25) | Al(4)–O(5) | 1.826(22) | C(5)–C(6) | 1.211(50) |
| Al(1)–O(4) | 1.908(19) | Al(4)–O(6) | 1.757(28) | C(7)–C(8) | 1.126(75) |
| Al(1)–O(5) | 1.863(20) | Al(4)–C(19) | 1.952(49) | C(9)–C(10) | 1.345(55) |
| Al(1)–O(6) | 1.862(25) | Al(4)–C(21) | 1.889(37) | C(11)–C(12) | 1.099(60) |
| Al(3)–O(3) | 1.752(24) | O(1)–C(1) | 1.423(44) | C(13)–C(14) | 1.031(74) |
| Al(3)–O(4) | 1.802(22) | O(2)–C(7) | 1.408(56) | C(15)–C(16) | 1.254(43) |
| Al(3)–C(11) | 1.968(43) | O(3)–C(9) | 1.284(53) | C(17)–C(18) | 1.325(46) |
| Al(3)–C(13) | 1.919(56) | O(4)–C(15) | 1.347(37) | C(19)–C(20) | 1.121(71) |
| Al(2)–O(1) | 1.811(22) | O(5)–C(17) | 1.272(38) | C(20)–C(22) | 1.109(63) |
| Al(2)–O(2) | 1.781(26) | O(6)–C(23) | 1.272(54) | C(23)–C(24) | 1.264(61) |
| O(1)–Al(1)–O(2) | 74.2(9) | O(1)–Al(2)–O(2) | 77.5(10) | | |
| O(1)–Al(1)–O(3) | 95.4(9) | O(1)–Al(2)–C(3) | 119.7(17) | | |
| O(2)–Al(1)–O(3) | 98.1(11) | O(2)–Al(2)–C(3) | 112.9(15) | | |
| O(1)–Al(1)–O(4) | 164.0(10) | O(1)–Al(2)–C(5) | 117.1(15) | | |
| O(2)–Al(1)–O(4) | 97.0(9) | O(2)–Al(2)–C(5) | 113.8(15) | | |
| O(3)–Al(1)–O(4) | 72.3(9) | O(3)–Al(2)–C(5) | 111.5(19) | | |
| O(1)–Al(1)–O(5) | 93.4(8) | C(5)–Al(4)–O(6) | 77.1(10) | | |
| O(2)–Al(1)–O(5) | 162.5(10) | O(5)–Al(4)–C(19) | 112.0(16) | | |
| O(3)–Al(1)–O(5) | 95.2(10) | O(6)–Al(4)–C(19) | 115.2(14) | | |
| O(4)–Al(1)–O(5) | 97.8(9) | Al(1)–Al(4)–C(21) | 125.8(12) | | |
| O(1)–Al(1)–O(6) | 98.4(10) | O(5)–Al(4)–C(21) | 116.2(13) | | |
| O(2)–Al(1)–O(6) | 95.7(11) | O(6)–Al(4)–C(21) | 116.5(15) | | |
| O(3)–Al(1)–O(6) | 162.7(11) | C(19)–Al(4)–C(21) | 114.6(17) | | |
| O(4)–Al(1)–O(6) | 95.7(10) | Al(1)–O(1)–Al(2) | 103.1(9) | | |
| O(5)–Al(1)–O(6) | 73.6(10) | Al(1)–O(1)–C(1) | 132.6(19) | | |
| O(3)–Al(3)–O(4) | 76.9(10) | Al(2)–O(1)–C(1) | 118.5(20) | | |
| O(3)–Al(3)–C(11) | 112.4(15) | Al(1)–O(1)–Al(2) | 105.2(11) | | |
| O(4)–Al(3)–C(11) | 113.6(14) | Al(1)–O(2)–C7 | 125.5(27) | | |
| O(3)–Al(3)–C(13) | 113.7(19) | Al(2)–O(2)–C7 | 129.0(29) | | |
| O(4)–Al(3)–C(13) | 116.4(19) | Al(1)–O(3)–Al(3) | 107.9(12) | | |
| C(11)–Al(3)–C(13) | 117.3(22) | Al(1)–O(3)–C(9) | 127.4(23) | | |
| Al(3)–C(3)–C(9) | 124.1(24) | | | | |
| Al(1)–O(4)–Al(3) | 102.9(10) | | | | |
| Al(1)–O(4)–C(15) | 133.3(20) | | | | |
| Al(3)–O(4)–C(15) | 123.4(20) | | | | |
| Al(1)–O(5)–Al(4) | 103.2(10) | | | | |
| Al(1)–O(5)–C-(17) | 131.7(20) | | | | |
| Al(4)–O(5)–C-(17) | 122.9(20) | | | | |
| Al(1)–O(6)–Al(4) | 106.0(11) | | | | |
| Al(1)–O(6)–C(23) | 132.3(27) | | | | |
| Al(4)–O(6)–C(23) | 120.1(26) | | | | |
| O(1)–C(1)–C(2) | 119.5(36) | | | | |
| Al(2)–C(3)–C(4) | 155.0(46) | | | | |
| Al(2)–C(5)–C(6) | 133.1(38) | | | | |
| O(2)–C(7)–C(8) | 123.1(50) | | | | |
| O(3)–C(9)–C(10) | 129.6(37) | | | | |
| Al(3)–C(11)–C(12) | 130.3(43) | | | | |

TABLE 4-continued

Bond Lengths (Å) Angles (°) for 2

| | |
|---|---|
| Al(3)–C(13)–C(14) | 138.2(59) |
| O(4)–C(15)–C(16) | 134.5(34) |
| O(5)–C(17)–C(18) | 131.6(31) |
| Al(4)–C(19)–C(20) | 127.8(43) |
| Al(4)–C(21)–C(22) | 140.4(39) |

TABLE 5

Summary of X-ray data for (1) and (2)

| Compound | 1 | 2 |
|---|---|---|
| Formula | $C_{18}H_{48}Al_4O_6$ | $C_{24}H_{60}Al_4O_6$ |
| Formula weight | 468.5 | 552.6 |
| Crystal System | Monoclinic | Monoclinic |
| Space Group | $P2_1/c$ | $P2_1/c$ |
| a (Å) | 11.646 (1) | 12.205 (2) |
| b (Å) | 11.444 (2) | 12.248 (1) |
| c (Å) | 22.759 (2) | 24.440 (2) |
| β (°) | 98.51 (1) | 98.75 (1) |
| V (Å$^3$) | 2999.9 (6) | 3611.3 (7) |
| Z | 4 | 4 |
| $D_{calc}$ (g/cm$^3$) | 1.037 | 1.016 |
| Crystal size (mm) | 0.7 × 0.4 × 0.4 | 0.5 × 0.5 × 0.5 |
| Temperature (K.) | 298 | 298 |
| 2θ range (deg) | 3.5–45 | 3.5–45 |
| Scan type | 2θ–θ | 2θ–θ |
| Scan speed (deg/min) | 10–60 | 8–60 |
| Scan range (deg) | 0.31 | 0.40 |
| Reflections collected | 5182 | 5182 |
| Indp Reflections | 3937 | 4754 |
| Obsd Reflections | 1588 | 1021 |
| | (F > 4.0 σ (F)) | (F > 4.0 σ (F)) |
| Number of Parameters | 253 | 307 |
| R | 0.0776 | 0.0896 |
| $R_W$ | 0.0765 | 0.0876 |
| GOF | 2.51 | 3.79 |
| LarDiff. Peak (e/Å$^3$) | 0.23 | 0.21 |

TABLE 6

Selected Bond Lengths and Angles for 1, 2 and Related Compounds

| Compound | O—Al$^6$-(Å) | O—Al$^4$-(Å) | O—Al$^6$—O (°) | O—Al$^4$—O (°) | Al—O—Al (°) |
|---|---|---|---|---|---|
| {Me$_2$Al(OEt)$_2$}$_3$Al (1) | 1.90 | 1.82 | 75.7 | 79.9 | 102.2 |
| {Et$_2$Al(OEt)$_2$}$_3$Al (2) | 1.87 | 1.79 | 73.4 | 77.1 | 104.7 |
| {O$^i$Pr$_2$Al(O$^i$Pr)$_2$}$_3$Al | 1.92 | 1.80 | 76.2 | 82.5 | 100.4 |
| [{(CH$_3$)$_2$Al(OCH$_2$-2C$_4$H$_3$S)$_2$}$_2$]$_3$Al | 1.91 | 1.83 | 76.2 | 79.9 | 102.2 |

TABLE 7

XRD and EA Date for the Decomposition of 1–3.

| Compound | Temperature | XRD | EA |
|---|---|---|---|
| 1 | 180 | amorph. | % C = 4.01 |
| | | | % H = 2.75 |
| | 300 | amorph. | % C = 2.35 |
| | | | % H = 2.05 |
| | 400 | amorph. | % C = 1.09 |
| | | | % H = 1.48 |
| 2 | 180 | amorph. | % C = 4.92 |
| | | | % H = 2.61 |
| | 300 | amorph. | % C = 2.90 |
| | | | % H = 2.08 |
| | 400 | amorph. | % C = 0.78 |
| | | | % H = 1.56 |
| 3 | 180 | amorph. | % C = 7.70 |
| | | | % H = 2.98 |
| | 300 | amorph. | % C = 3.82 |
| | | | % H = 2.17 |
| | 400 | amorph. | % C = 0.81 |
| | | | % H = 1.77 |

Now by using the methods and compounds of this invention one can make solid aluminum oxide, especially in the form of films, coatings and powders without requiring high temperatures or gas phase deposition. Althouth the invention has been described in detail with reference to certain embodiments, it will be appreciated by those skilled in the art that there are other embodiments within the spirit and the scope of the claims.

EXAMPLE 3

Deposition studies were carried out by applying a coat of precursor oil onto a metallic substrate followed by 90 minutes of heating at a specified temperature.

Table 7 shows the X-ray diffraction (XRD), and elemental analyses (EA) for deposits obtained from oils 1, 2 and 3 at temperatures of 180° C., 300° C. and 400° C. At these low temperatures the oils do not produce crystalline materials as evidenced by the absence of an XRD pattern.

The EA data demonstrate that in all three cases the organic ligands are almost entirely eliminated and that aluminum oxide can be obtained, at low temperatures, from the single source precursors disclosed herein. This presents further support that the films formed upon the original decomposition of the precursors are amorphous alumina.

What is claimed is:

1. A single source precursor process for making an inorganic material comprising:
    (a) providing an organometallic compound having at least one organic ligand and a 2:3 stoichiometric ratio between aluminum and oxygen; and
    (b) decomposing said organometallic compound to eliminate the organic ligand and to produce an amorphous aluminum oxide having a 2:3 stoichiometric ratio between said aluminum and said oxygen.

2. The process of claim 1 wherein decomposing said organometallic compound is by pyrolysis.

3. The process of claim 1 wherein decomposing said organometallic compound is by photolysis.

4. The process of claim 1 wherein the inorganic material is in the form of a coating, film or powder.

5. The process of claim 4 wherein prior to decomposing said organometallic compound is applied onto a substrate.

6. Inorganic materials produced by the process of claim 1.

7. A process for making aluminum organometallic compounds comprising:
   (a) mixing a triorganometallic compound of aluminum with a triorganooxymetallic compound of said aluminum in a solvent medium to form a reaction mixture;
   (b) heating the reaction mixture at reflux temperature thereby reacting said triorganometallic compound with said triorganooxymetallic compound; and
   (c) isolating from said solvent medium an aluminum organometallic compound having an aluminum to oxygen stoichiometric ratio of 2:3.

8. The process of claim 7 wherein the aluminum organometallic compound has a tetrametallic structure.

9. The process of claim 7 wherein the triorganometallic compound is triorganoaluminum and the triorganooxymetallic compound is triorganooxyaluminum.

10. The process of claim 9 wherein the triorganooxyaluminum compound is triethoxyaluminum.

11. The process of claim 9 wherein the reaction mixture is formed and maintained under an inert atmosphere and the heating is carried out for a period of time sufficient to react the triorianoaluminum compound with the triorganooxyaluminum compound.

12. The process of claim 9 further comprising mixing the aluminum organometallic compound with a chemically distinct organoaluminum compound, said chemically distinct organoaluminum compound having an aluminum to oxygen stoichiometric ratio of 2:3.

13. The process of claim 7 wherein the aluminum organometallic compound is a viscous liquid.

* * * * *